United States Patent [19]
Kumar

[11] Patent Number: 5,336,869
[45] Date of Patent: Aug. 9, 1994

[54] METHOD AND APPARATUS FOR MANIPULATING FLUID

[76] Inventor: M. Lalith Kumar, 457 Dover Dr., Pittsburgh, Pa. 15238

[21] Appl. No.: 800,572

[22] Filed: Nov. 27, 1991

[51] Int. Cl.$^5$ .............................................. H05B 6/00
[52] U.S. Cl. .................................. 219/687; 219/688; 604/9; 604/247
[58] Field of Search .................. 219/10.55 A, 10.55 R, 219/10.55 D, 10.55 F, 10.55 M, 10.65, 10.57, 8.5, 10.491, 10.51, 10.53, 687, 688; 210/634, 643, 656, 198.2; 422/70, 256; 137/316; 423/659; 123/472; 138/93; 604/9, 247

[56] References Cited

U.S. PATENT DOCUMENTS

| | | | |
|---|---|---|---|
| 2,978,562 | 4/1961 | Fox | 219/10.55 A |
| 3,778,578 | 12/1973 | Long et al. | 219/10.55 A |
| 3,794,801 | 2/1974 | Long et al. | 219/10.55 A |
| 3,920,945 | 11/1975 | Smith et al. | 219/10.55 R |
| 3,999,575 | 12/1976 | Bernard | 137/807 |
| 4,358,652 | 11/1982 | Kaarup | 219/10.55 A |
| 4,417,116 | 11/1983 | Black | 219/10.55 A |
| 4,434,765 | 3/1984 | Eshelman | 123/472 |
| 4,458,721 | 7/1984 | Yie et al. | 138/93 |
| 4,524,743 | 6/1985 | McAuliffe et al. | 123/438 |
| 4,627,832 | 12/1986 | Hooven et al. | 604/9 |
| 4,741,448 | 5/1988 | Alley et al. | 215/266 |
| 4,776,838 | 10/1988 | Sainte-Rose et al. | 604/9 |
| 5,080,128 | 1/1992 | Taylor | 137/316 |
| 5,094,753 | 3/1992 | Allington et al. | 210/634 |
| 5,098,690 | 3/1992 | Koves | 423/659 |

Primary Examiner—Bruce A. Reynolds
Assistant Examiner—Tu Hoang
Attorney, Agent, or Firm—Ansel M. Schwartz

[57] ABSTRACT

The present invention is an apparatus for manipulating fluid flow. The apparatus includes a member having a channel through which fluid flows and at least one opening of a predetermined diameter in communication with the channel. The opening controls the fluid flow thereacross. At least a portion of the member is in thermal contact with the opening and is made of a material reactive with electromagnetic energy. There is also a device for providing electromagnetic energy. The providing device is in communication with the portion of the member reactive to electromagnetic energy such that the electromagnetic energy heats the portion of the member. The present invention also pertains to an apparatus for restricting fluid flow. The restricting apparatus includes a member having a first surface, a second surface opposing the first surface and an opening between the first and second surface for restricting the fluid flow therethrough. The member is made of sapphire or ruby. Preferably, the opening has a first diameter at the top surface and a second diameter at the bottom surface, the first diameter is greater than the second diameter. The present invention also pertains to a method of manipulating fluid flow. The method comprises the first step of heating with electromagnetic radiation a fluid restrictor, followed by the step of flowing fluid through the restrictor.

13 Claims, 3 Drawing Sheets

METHOD AND APPARATUS FOR MANIPULATING FLUID

FIELD OF THE INVENTION

The present invention is related in general to the manipulation of fluid flow. More specifically, the present invention is related to a fluid restrictor which is heated with electromagnetic radiation.

BACKGROUND OF THE INVENTION

In many applications using supercritical fluids, the fluid has to be depressurized after extraction or chromatography. A restrictor is typically used to restrict the flow and/or depressurize the fluid. There are a number of different kinds of restrictors and some of them are: a) a plain tube that is crimped, b) a tube that is heated and tapered to reduce the inside diameter (Chester, T. L., Innis, D. P. and Owens, G. D., Anal Chem., 57, 1985, 2243–2247), c) an integral restrictor: where you melt the end of tubing to close it shut and then grind it to give the proper size hole (Guthrie, E. J. and Schwatz, H. E., J. Chromatographic Sci., 24, 1986, 236–241), d) a metal orifice restrictor where a laser drilled hole serves as the restrictor (Randall, L. G. and Wahrfartig, A. L., Anal. Chem. 50, 1978, 1703–1705), and e) a valve (Sin, C. H. et al., Anal. Chem., 58, 1986, 487–490). When a fluid such as carbon dioxide depressurizes, it cools and sometimes solidifies, plugging the restrictor (Dick, R. D., et al., Anal. Chem., 58, 1986, 2057–2064). To alleviate this situation, heat is usually supplied through an external device. This is usually achieved through a resistive heating tape or cartridge near the restrictor.

These current restrictor technologies have a number of problems. A crimped tube cannot be manufactured reproducibility and can plug easily (Smith, R. D., Fjeldsted, J. C., and Lee, M. L., Chromatogr. 247, 1982, 241–243). A tapered tube does not plug as easily, however, it is difficult to manufacture and very fragile (Smith, R. D., et al., Anal. Chem., 55, 1983, 2266–2272) and since they are typically made out of fused silica, they are poor conductors of heat. Similar to the tapered restrictors, the integral restrictors are poor conductors of heat and plug often (Wright, B. W. and Smith, R. D., Modern Supercritical Fluid Chromatography, Ed. White, C. M., Huthig, 1988, 189–210). A metal orifice restrictor offers easy replacement, but the flow varies depending how it is assembled (Dick, R. D., et al., Anal. Chem., 58, 1986, 2057–2064). Further, the temperature control algorithm causes changes in flow rate due to the high thermal expansion. With respect to a valve, it has a high dead volume which reduces the efficiency and accuracy of the system.

In supercritical fluid extraction, the restrictors are used to collect the soluble analytes for further processing. Typically, a solvent is used for collecting the soluble analytes. Heating the restrictor is necessary to stop it from plugging during operation. Heating the restrictor by heating the solvent is not a viable solution since the low boiling point of the solvent leads to vaporization of the solvent and therefore inaccuracies in the result. Therefore, there is a need for heating the restrictor non-invasively. Further, a restrictor is needed which is comprised of a hard material that will not erode easily and will not change shape easily under pressure and has a low coefficient of thermal expansion and a high thermal conductivity.

SUMMARY OF THE INVENTION

The present invention is an apparatus for manipulating fluid flow. The apparatus includes a member having a channel through which fluid flows and at least one opening of a predetermined diameter in communication with the channel. The opening controls the fluid flow thereacross. At least a portion of the member is in thermal contact with the opening and is made of a material reactive with electromagnetic energy. There is also means for providing electromagnetic energy. The providing means is in communication with the portion of the member reactive to electromagnetic energy such that the electromagnetic energy heats the portion of the member. Preferably, the member includes a restrictor having the opening and in thermal contact with the electromagnetically reactive portion and the providing means includes means for producing electromagnetic radiation.

In a preferred embodiment, the restrictor is made of ruby or sapphire and the member has an end in which said restrictor is fixedly disposed. The end is made of electromagnetically reactive material. The end can include a cap which holds the restrictor in place, or can have a pocket which holds the restrictor in place.

The apparatus can include means for collecting the fluid and means includes means for cooling the collecting means. The collecting means can include a container or a collection surface. Preferably, at least the electromagnetically reactive portion of the member, the means for providing electromagnetic energy and the collection means are enclosed within an electromagnetic shield. In a preferred embodiment, the opening is tapered.

The present invention also pertains to an apparatus for restricting fluid flow. The restricting apparatus includes a member having a first surface, a second surface opposing the first surface and an opening between the first and second surface for restricting the fluid flow therethrough. The member is made of sapphire or ruby. Preferably, the opening has a first diameter at the top surface and a second diameter at the bottom surface, said first diameter greater than said second diameter.

The present invention also pertains to a method of manipulating fluid flow. The method comprises the first step of heating with electromagnetic radiation a fluid restrictor, followed by the step of flowing fluid through the restrictor. Preferably, after the flowing step, there is the step of collecting the fluid in a container filled with solvent.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
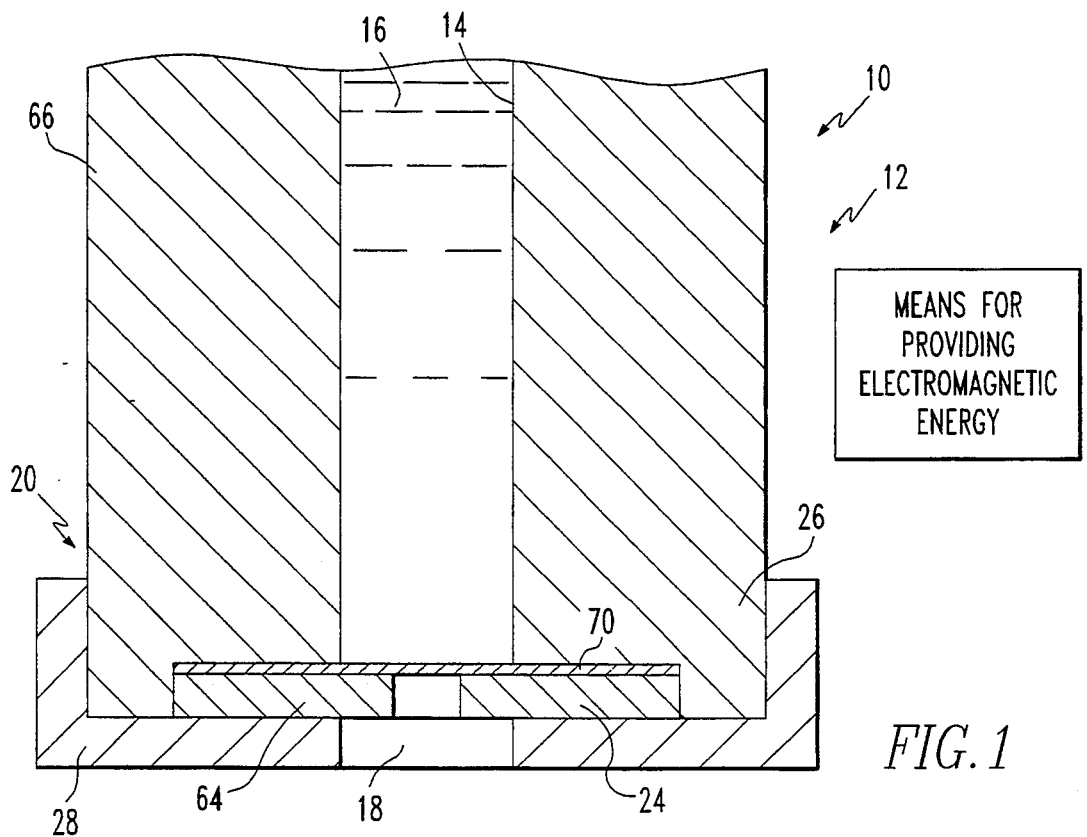
FIG. 1 is a schematic representation showing an apparatus for manipulating fluid flow.

Referring now to the drawings wherein like reference numerals refer to similar or identical parts throughout the several views, and more specifically to FIG. 1 thereof, there is shown an apparatus 10 for manipulating fluid flow. The apparatus 10 has a member 12 having a channel 14 through which fluid 16 flows and at least one opening 18 of a predetermined size in communication with the channel 14 which controls the flow of fluid 16. At least a portion 20 of the member 12 is in thermal contact with the opening and is made of a material which is reactive with electromagnetic energy. There is also means 22 for providing electromagnetic energy which is in communication with the portion 20 of the member 12 reactive to electromagnetic energy such that the electromagnetic energy heats the portion 20 of the member 12. The fluid 16 is preferably a supercritical fluid such as $CO_2$, water $NH_3$, pentane, ethylene or freon. The fluid 16 can be pressurized up to 700 atmospheres at temperatures up to 400° C. The means for providing electromagnetic energy can be any suitable device which causes the portion of the member in thermal contact with the opening to be heated non-invasively. A magnetron can be used for providing microwave radiation or RF coils can be used for providing high frequency induction heating.

Figure 2:
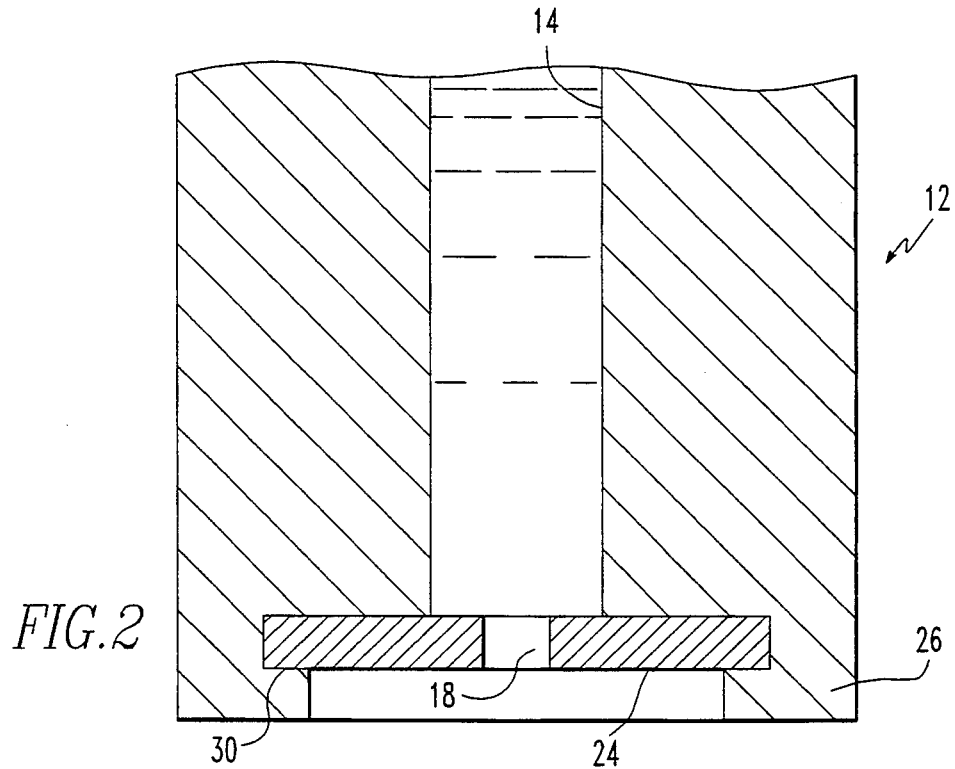
FIG. 2 is a schematic representation showing an alternative embodiment of the apparatus for manipulating fluid flow.

In a preferred embodiment, the member 12 includes a restrictor 24 having the opening 18 which is in thermal contact with the electromagnetically reactive portion 20. The restrictor 24 is preferably a disk 64 made of a material having a low coefficient of thermal expansion and a high thermal conductivity such as ruby or sapphire. The disk 64 can range in diameter between 0.4 to 50 mm or greater and can have a thickness of 0.1 to 0.5 mm or greater. The opening 18 can range from 0.5 to 500 microns or greater. The member 12 has an end 26 in which the restrictor 24 is fixedly disposed. The end 26 is made of electromagnetically reactive material. Preferably, the end 26 includes a cap 28 which holds the restrictor 24 in place. The cap 28 can be made of magnetically permeable material such as permalloy or of a microwave absorbing material such as silicon carbide. Alternatively, as shown in FIG. 2, the end can be crimped to define a pocket 30 which holds the restrictor in place. A gasket 70 can be used to seal the restrictor 24 to the channel 14. The gasket 70 can be made of teflon, vespel or other polymers.

Figure 3A:
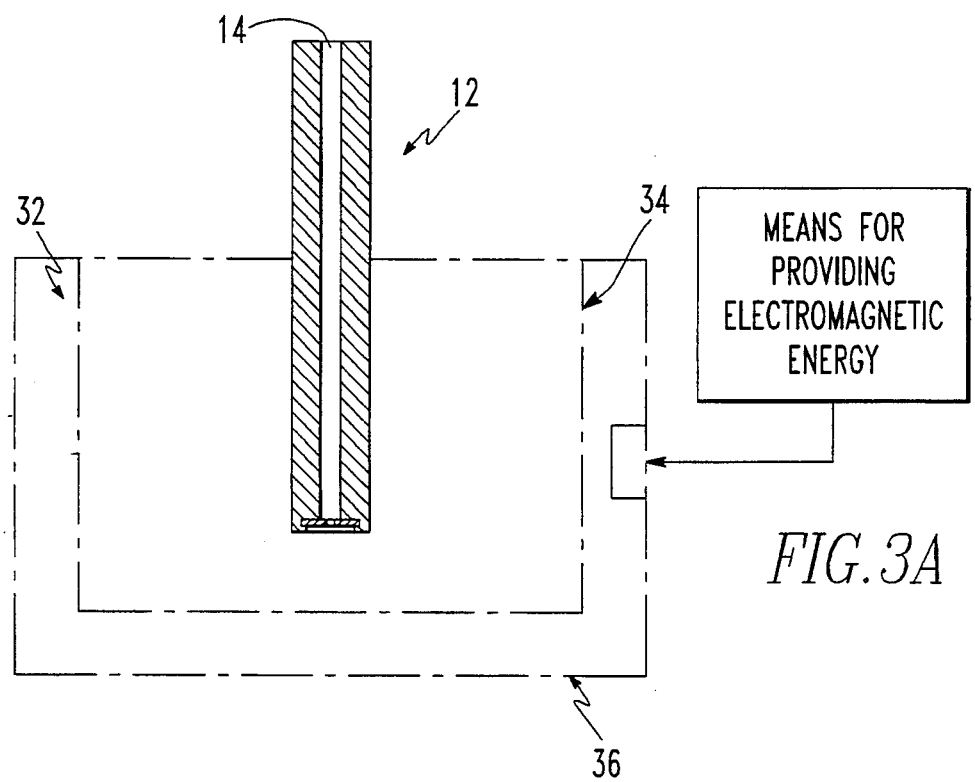
FIG. 3a is a schematic representation showing a preferred embodiment of the apparatus for manipulating fluid flow.
Figure 3B:
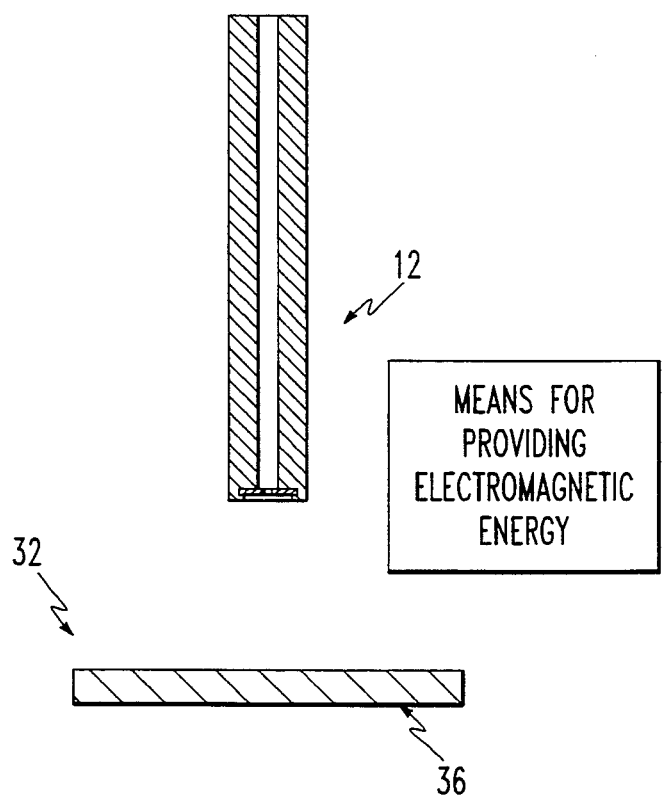
FIG. 3b is a schematic representation showing the apparatus for manipulating fluid flow having a collecting surface.
Figure 4:
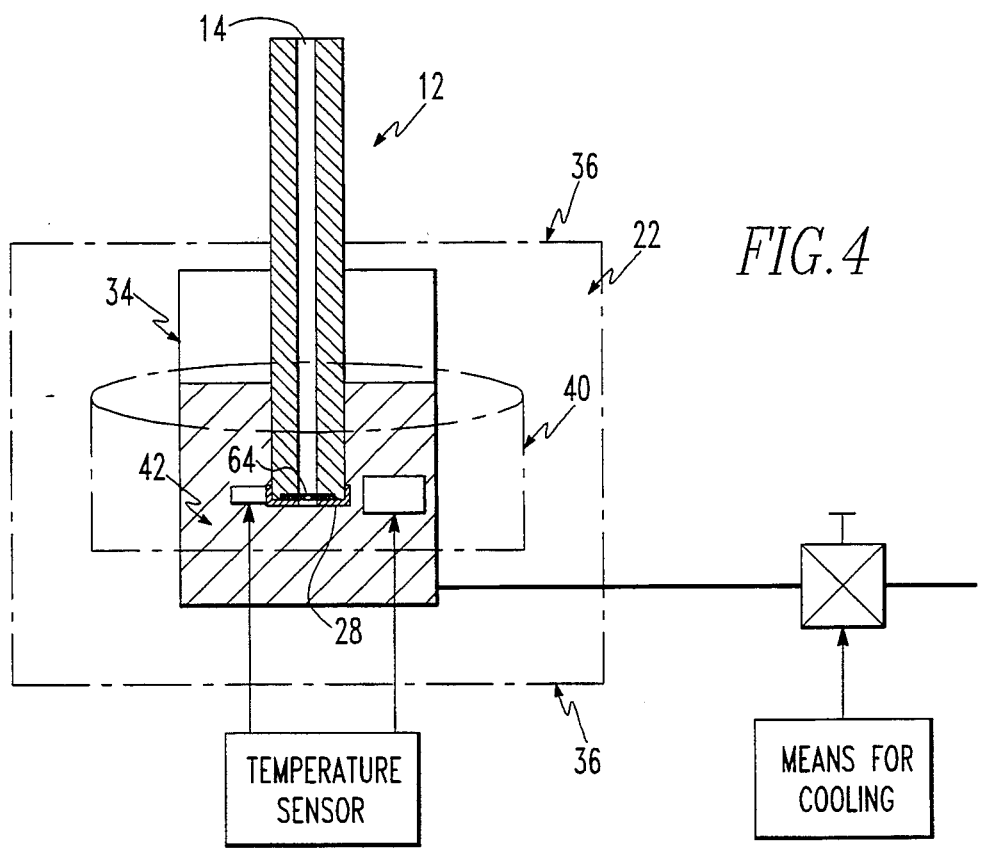
FIG. 4 is a schematic representation showing a preferred embodiment of the apparatus for manipulating fluid flow.

As shown in FIG. 3a, the apparatus can include means 32 for collecting the fluid, such as a container 34. The container 34 can hold a solvent 42 through which the fluid 16 is bubbled, thereby removing the analyte from the fluid 16. The solvent 42 can be, for example, methanol, methylene chloride or hexane. The container 34 and surface 36 can be made of glass, teflon or epoxy. Alternatively, as shown in FIG. 3b, the collecting means 32 can be a collection surface 36. When the fluid is depressurized, the analytes are precipitated from the supercritical phase. The depressurized fluid and the precipitated analytes hit the collection surface and collect in the form of a dry powder. In some instances, lowering the temperature of the collection surface improves the efficiency of collection and reduces the probability of agglomeration of fine powders into lumps. Preferably, at least the electromagnetically reactive portion 20 of the member 12, the means for providing electromagnetic energy 22 and the collection means 32 are enclosed within an electromagnetic shield 36. The means for providing electromagnetic 22 energy can include a microwave generator or induction coils 40 as shown in FIG. 4. Preferably, a temperature sensor 42 is disposed adjacent to the electromagnetically reactive portion 20 of the member 12 for monitoring its temperature. The output of the temperature sensor 42 can be in communication with the means 22 for providing electromagnetic energy. Preferably, as shown in FIG. 4, the collecting means 32 includes means for cooling the container 34 and a temperature sensor to monitor the container's temperature. The cooling means can use carbon dioxide or be a standard refrigeration system.

Figure 5:
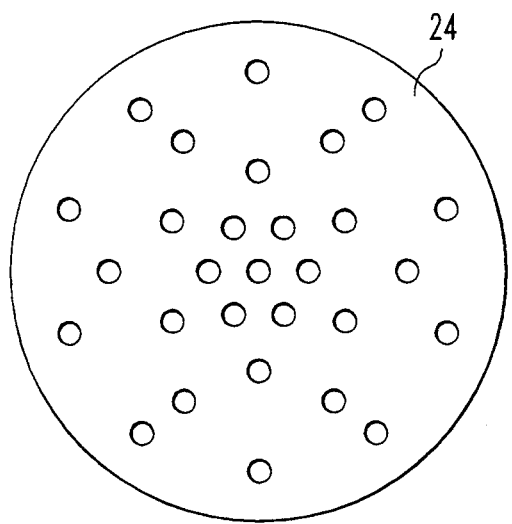
FIG. 5 is a schematic representation showing the restrictor disk with multiple openings.

As shown in FIG. 5, the restrictor 24 can have a plurality of openings 18 arranged in a radial pattern. The number and size of the openings determine the level of fluid restriction. Each opening 18 can be tapered to help prevent clogging.

The present invention also relates to a method for manipulating the fluid flow. The method comprises the first step of heating with electromagnetic radiation at least a portion of a fluid restrictor; followed by the step of flowing fluid through the restrictor. Preferably, after the flowing step, there is the step of collecting the fluid.

Figure 6:
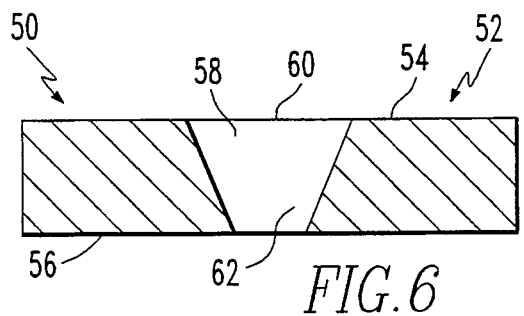
FIG. 6 is a schematic representation showing a cross section of the restrictor.

As shown in FIG. 6, the present invention is also related to an apparatus 50 for restricting fluid flow. The apparatus 50 includes a member 52 having a first surface 54, a second surface 56 disposed in an opposing relationship with the first surface 54 and an opening 58 between the first and second surfaces for restricting fluid flow therethrough. The member 12 is made of a material having a low coefficient of thermal expansion and high thermal conductivity, such as sapphire or ruby. The low coefficient of thermal expansion ensures that the opening essentially does not change in size much due to temperature variations, while the high thermal conductivity provides for efficient heat transfer. Preferably, the opening 58 has a first diameter 60 at the first surface 54 and a second diameter 62 at the second surface 54 wherein the first diameter is greater than the second diameter. This tapered profile helps to prevent clogging of the opening 58.

In the operation of the apparatus 10 and as shown in FIG. 1, the restrictor is a disk 64. The disk 64 is drilled using a laser to form the opening 18. The disk material has the properties of low thermal expansion and high thermal conductivity. The disk 64 is made of sapphire of 1 mm diameter and 0.25 mm thick having an opening 18 of 3 micron. The restrictor disk 64 is mounted in a stainless steel tube 66 having a length of 60 mm. The disk 64 is held within the tube 66 with the cad 28. The diameter of the disk 64 should be greater than the ID of the tube 66 and preferably not greater than the OD of the tube 66. The cap 28 is also made of stainless steel. The 1 mm round and a 0.25 mm thick disk 64 with a 0.03 micron opening 18 is mounted in a 1/16" O.D. tube 66 with a 0.020" ID by counterboring it to a depth of 0.25 mm. The cap 28 coated with silicon carbide with an outside diameter of 2.5 mm and an inside diameter of 1/16" and a height of 5 mm is fitted over the 1/16" tube to hold the disk 64. The cap 28 is fitted by being pressed onto the 1/16" tube 28. To prevent leakage of the fluid through the side of disk 64, a gasket 70 is provided. The gasket is made a high temperature polymer such as teflon.

During operation, and as shown in FIG. 4, the fluid 16 which is supercritical $CO_2$ pressurized to 700 atmospheres and having the preferred analyte dissolved within flows through the channel 14 of member 12. In order to exit the channel 14, the $CO_2$ must pass through the 3 micron opening 18 formed through the sapphire disk 64. This restriction causes a pressure loss within the $CO_2$ after passing through the opening 18. According to Boyle's law, this pressure loss is accompanied by a temperature drop within the $CO_2$ which can cause it to freeze, thus clogging the opening 18. Inductive coils 40 surround the cap 28 and provide electromagnetic radiation which heat the silicon carbide coating of the cap 28. The sapphire disk 64 which is in thermal contact with the cap 28 is in turn heated. In this manner, heat is supplied to the opening 18 to prevent the $CO_2$ from freezing and clogging the opening 18. A temperature sensor monitors the temperature of the cap 28 and/or disk 64.

After leaving the opening 28, the $CO_2$ is bubbled through a solvent of methylene chloride which collects the analyte from the $CO_2$. To prevent the methylene chloride from evaporating, a cooling system is provided. A temperature sensor is disposed about the container 34 to monitor the temperature of the methylene chloride. The entire system of the container 34, the member 12 and the induction coils 40 are enclosed in an electromagnetic shield 36 to prevent the electromagnetic radiation produced by the induction coils 70 from escaping.

When the fluid is depressurized, the analytes are precipitated from the supercritical phase. The depressurized fluid and the precipitated analytes hit the collection surface and collect in the form of a dry powder. In some instances, lowering the temperature of the collection surface improves the efficiency of collection and reduces the probability of agglomeration of fine powders into lumps. As shown in FIG. 3b, the collection of an analyte in the form of a powder can be achieved by replacing the container 34 with a passivated collection surface 36 which can be cooled, if necessary. After passing through the opening 18, the powder is collected on the surface 36.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for manipulating fluid flow comprising:
   a member having a channel through which fluid flows, said member having a restrictor having at least one opening of a predetermined diameter in communication with the channel, said restrictor controlling the fluid flow thereacross, at least a portion of said restrictor in thermal contact with the opening and made of a material reactive with electromagnetic energy, said restrictor comprised of ruby or sapphire; and
   means for providing electromagnetic energy, said providing means in communication with said portion of the member reactive to electromagnetic energy wherein the electromagnetic energy heats the portion of the member.

2. An apparatus as described in claim 1 wherein the electromagnetic energy providing means includes means for producing electromagnetic radiation, and wherein the material reactive with electromagnetic energy is reactive to electromagnetic radiation.

3. An apparatus as described in claim 2 wherein the member has an end in which said restrictor is fixedly disposed, said end made of electromagnetically reactive material.

4. An apparatus as described in claim 3 wherein said end includes a cap which holds the restrictor in place.

5. An apparatus as described in claim 3 wherein the end has a pocket which holds the restrictor in place.

6. An apparatus as described in claim 4 including means for collecting the fluid.

7. An apparatus as described in claim 6 wherein said collecting means includes means for cooling the collecting means.

8. An apparatus as described in claim 7 wherein said collecting means includes a container.

9. An apparatus as described in claim 7 wherein said collecting means includes a collection surface.

10. An apparatus as described in claim 7 wherein at least the portion of said restrictor reactive with electromagnetic radiation and the means for producing electromagnetic radiation and the fluid collecting means are enclosed within an electromagnetic shield.

11. An apparatus as described in claim 7 wherein said opening is tapered.

12. An apparatus as described in claim 11 wherein the restrictor has a plurality of openings.

13. An apparatus as described in claim 12 wherein the electromagnetic radiation producing means includes means for producing microwaves.

* * * * *